United States Patent [19]

Paul et al.

[11] 4,048,166
[45] Sept. 13, 1977

[54] 3-CARBOALKOXY (OR PHENOXY) AND 3-THIOCARBO-(3-CHLORO-2-PROPENYL)-1,3,5,7-TETRAAZABICYCLO(3.3.1)NONANE AND PREPARATION

[75] Inventors: Albertha M. Paul, Holliston, Mass.; Charles E. Moppett, Mystic, Conn.

[73] Assignee: The Dow Chemical Company, Midland, Mich.

[21] Appl. No.: 741,089

[22] Filed: Nov. 11, 1976

[51] Int. Cl.$^2$ .................. C07D 257/10; C07D 519/00
[52] U.S. Cl. ..................................... 544/215; 424/249
[58] Field of Search ..................... 260/248 NS

[56] References Cited

U.S. PATENT DOCUMENTS

| | | | |
|---|---|---|---|
| 3,862,939 | 1/1975 | Brady | 260/248 NS |
| 3,862,940 | 1/1975 | Mitchell et al. | 260/248 NS |

*Primary Examiner*—John M. Ford
*Attorney, Agent, or Firm*—Theodore Post; C. Kenneth Bjork

[57] ABSTRACT

Compounds of the formula

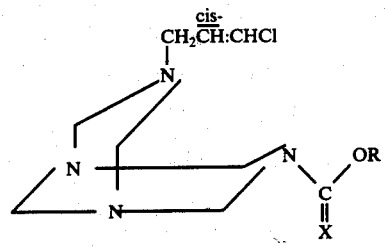

where X represents O or S and R represents $C_{1-4}$ alkyl, phenyl or ($C_{1-4}$ alkyl)phenyl. The compounds are prepared by reacting the ring-opened intermediate, obtained by reacting cis-1-(3-chloro-2-propenyl)-3,5,7-triaza-1-azoniatricyclo (3.3.1.1$^{3,7}$) decane chloride with excess aqueous sodium hydroxide, with an equivalent amount of a corresponding halide formate or halide thioformate, ClC=X(OR), at about 0° C in the presence of a hydrogen chloride acceptor and using a non-nucleophilic organic solvent as reaction medium. The carbamate products have antimicrobial utility.

5 Claims, No Drawings

3-CARBOALKOXY (OR PHENOXY) AND 3-THIOCARBO-(3-CHLORO-2-PROPENYL)-1,3,5,7-TETRAAZABICYCLO(3.3.1)NONANE AND PREPARATION

SUMMARY OF THE INVENTION

This invention concerns novel 3-carboalkoxy (or phenoxy) and 3-thiocarboalkoxy (or phenoxy) derivatives of 7-cis-(3-chloro-2-propenyl)-1,3,5,7-tetraazabicyclo(3.3.1)nonane corresponding to the formula

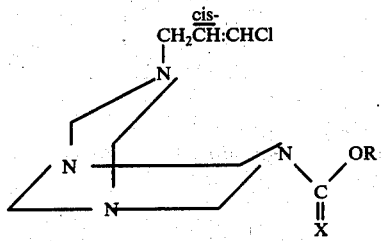

wherein X represents O or S and R represents $C_{1-4}$ alkyl, phenyl or $(C_{1-4})$alkylphenyl. The compounds are viscous oils, readily soluble in organic solvents.

The compounds are prepared in a 2-step process wherein cis-1-(3-chloro-2-propenyl)-3,5,7-triaza-1-azoniatricyclo(3.3.1.1$^{3,7}$)decane chloride, commercially available as Dowicil$^{(R)}$ 200 antimicrobial, is treated with excess aqueous sodium hydroxide to give the ring-opened intermediate, hereinafter "basic oil", as follows:

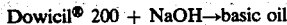

Excess sodium hydroxide, preferably, 4 molar proportions, is dissolved in water and cooled to room temperature. A quantity of about one mole of Dowicil® 200 antimicrobial is added slowly to the caustic solution and the reaction mixture is stirred approximately 15 minutes at ambient temperature. The basic oil which forms is extracted with benzene, the extract is dried over sodium sulfate and the benzene is evaporated to give the basic oil in an approximately 78% yield as a viscous oil.

In the second step, the indicated carbamate derivatives are prepared by reacting the basic oil with a halide formate or halide thioformate according to the following scheme:

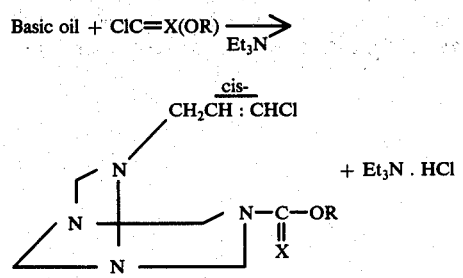

In the equation, X and R have the meanings previously given. In the above second step, one equivalent of halide formate or halide thioformate is added to any excess of basic oil, both such reactants being dissolved in an inert, anhydrous non-nucleophilic solvent such as acetone, ether, benzene, tetrahydrofuran, petroleum ether, diglyme, etc. A hydrogen halide acceptor such as triethylamine is present in excess in the reaction medium. The reaction temperature is maintained at about 0° C. The carbamate product forms almost immediately and the reaction is completed in about half an hour. The viscous oily product is separated from precipitated amine hydrochloride by-products by filtration and solvent is evaporated to leave the product. The product is identified by elemental analysis and by nuclear magnetic resonance.

DESCRIPTION OF SOME PREFERRED EMBODIMENTS

The following examples and teachings additionally describe specific embodiments and the best mode contemplated by the inventors of carrying out the invention.

Preparation A: Preparation of Basic Oil Intermediate

A quantity of 80 g (2.0 mole) of NaOH was dissolved in 500 ml water and cooled to room temperature. 100 Grams (0.4 mole) of Dowicil$^{(R)}$ 200 antimicrobial was added slowly to the caustic solution and the reaction mixture stirred ca. 15 minutes at ambient temperature. Extraction with benzene, drying over $Na_2SO_4$ and evaporation of the benzene gave 72 g (78% yield) of the basic oil, described above, as a viscous oil.

EXAMPLE 1

3-(Carbomethoxy)-7-cis-(3-chloro-2-propenyl)-1,3,5,7-tetraazabicyclo(3.3.1)nonane 10.0 Grams (0.043 mol) basic oil intermediate was dissolved in 50 ml dry ether and filtered through Celite$^{(R)}$. 4.35 Grams (0.043 mol) freshly distilled triethylamine (phenyl isocyanate was added to the distillation flask to remove primary and secondary amines) was dissolved in 50 ml dry ether and added to the basic oil solution. The mixture was cooled to 0° C. 3.87 Grams (0.043 mol) methyl chloroformate was dissolved in 25 ml dry ether and added slowly to the cold basic oil-triethylamine solution while stirring. A white precipitated formed immediately and the reaction was complete in 30 minutes. The precipitate was identified (NMR) as triethylamine-hydrogen chloride and was removed from the reaction mixture by filtration. The filtrate was evaporated on a rotary evaporator to give 7.85 g (70.2% yield) of a viscous oil identified (NMR) as the methyl carbamate derivative having the structure given above (X = O, R = $CH_3$). Elemental analysis is consistent with the given structure.

EXAMPLE 2

The procedure of Example 1 when repeated substituting an equivalent weight of the indicated ether halide formates or halide thioformates gave the following products:

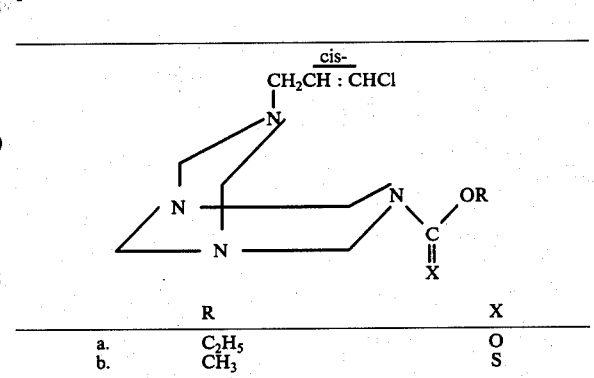

|   | R | X |
|---|---|---|
| a. | $C_2H_5$ | O |
| b. | $CH_3$ | S |

-continued

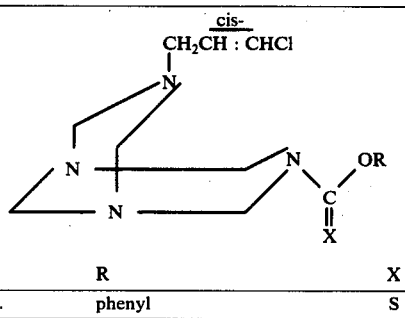

| | R | X |
|---|---|---|
| c. | phenyl | S |

All of the compounds of the invention are useful as antimicrobials for the control of bacteria and fungi. This is not to suggest that the compounds and their mixtures are equally effective against all such organisms at the same concentration. For such uses the compounds or their mixtures can be employed in an unmodified form or dispersed in water with the aid of a surface-active agent and the resulting emulsions employed as sprays. In other procedures, the products can be employed as active constituents in solvent solutions, oil-in-water or water-in-oil emulsions, including cosmetic emulsions. The augmented compositions are adapted to be formulated as concentrates and subsequently diluted with additional liquid or solid adjuvant to produce the ultimate treating compositions. Good results are obtained when employing compositions containing antimicrobial concentrations and usually from about 100 to 1,000 parts by weight of one or more of the compounds per million parts of such compositions.

Incorporation of the compounds of this invention into materials which are subject to bacterial and/or fungal attack inhibits the growth of such microbes and preserves the original value of the materials. The compounds are sufficiently non-volatile and water-insoluble that they will persist on or in such materials for long periods of time. Examples of materials which are adversely effected by fungal growth are latex paint films, wood and wooden products. The inventive compounds are sufficiently active against fungi that only small quantities are required to prevent mildew on paint films or wood rot. The compounds are therefore useful for long-term protection against fungal growth in or on materials having a wood basis or a protective or decorative paint film subject to fungal attack.

In representative conventional in vitro agar Petri dish dilution tests for determining minimum inhibitory concentrations (MIC) against the following organisms at the indicated concentrations in parts per million, the activity of the compounds of the examples was as follows:

MIC, ppm, of Examples:

| | 1 | 2a | 2c |
|---|---|---|---|
| S. aureus | 500 | 500 | 500 |
| E. coli | 500 | 500 | 500 |
| T. mentagrophytes | 100 | 100 | 100 |
| B. subtilis | 500 | 500 | 100 |
| E. aerogenes | 500 | 500 | 500 |
| C. pelliculosa | 500 | 500 | 500 |
| P. pullulans | 500 | 500 | 500 |
| S. typhosa | 100 | 100 | 100 |
| Ps. Species Strain 10 | 500 | 500 | 500 |
| M. phlei | 500 | 500 | 500 |
| R. nigricans | 500 | >500 | 500 |

What is claimed is:
1. A compound corresponding to the formula

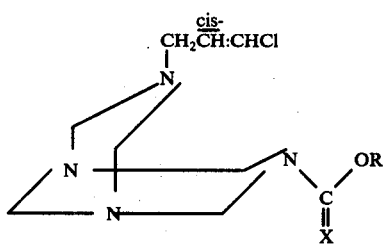

wherein X represents O or S and R represents $C_{1-4}$ alkyl, phenyl or ($C_{1-4}$ alkyl)phenyl.

2. The compound of claim 1 wherein X represents S and R represents phenyl.

3. The compound of claim 1 wherein X represents O and R represents methyl.

4. The compound of claim 1 wherein X represents O and R represents ethyl.

5. Method for making a 3-carboalkyl-, a 3-carbophenoxy-, a 3-thiocarboalkoxy- or a 3-thiocarbophenoxy-7-cis-(3-chloro-2-propenyl)-1,3,5,7-tetraazabicyclo(3.3.1)nonane which comprises reacting (A) a chloride formate or a chloride thioformate having the formula ClC=X(OR) wherein X is O or S and R is $C_{1-4}$ alkyl, phenyl or ($C_{1-4}$ alkyl)phenyl dissolved in an inert anhydrous non-nucleophilic organic solvent to (B) a solution in a similar solvent of excess of the reaction product of Dowicil(R) 200 with excess aqueous sodium hydroxide at a reaction temperature of about 0° C in the presence of excess of a hydrogen chloride acceptor and recovering the said product from the reaction medium.

* * * * *